United States Patent
Mattila

(10) Patent No.: US 8,961,874 B2
(45) Date of Patent: Feb. 24, 2015

(54) HEAT RECOVERY IN BIOWASTE STERILIZATION

(75) Inventor: Juha Mattila, Porvoo (FI)

(73) Assignee: Steris Europe, Inc. Suomen sivuliike, Tuusula (FI)

( * ) Notice: Subject to any disclaimer, the term of this patent is extended or adjusted under 35 U.S.C. 154(b) by 914 days.

(21) Appl. No.: 13/159,492

(22) Filed: Jun. 14, 2011

(65) Prior Publication Data

US 2012/0003120 A1  Jan. 5, 2012

(30) Foreign Application Priority Data

Jul. 2, 2010 (FI) ................... 20105757 U

(51) Int. Cl.
 *A61L 11/00* (2006.01)
 *C02F 1/02* (2006.01)
 *C02F 103/00* (2006.01)

(52) U.S. Cl.
 CPC . *A61L 11/00* (2013.01); *C02F 1/02* (2013.01); *C02F 2103/003* (2013.01); *C02F 2209/02* (2013.01); *C02F 2209/03* (2013.01); *C02F 2209/42* (2013.01); *C02F 2301/066* (2013.01); *C02F 2303/04* (2013.01); *C02F 2303/10* (2013.01)
 USPC ................ 422/38; 422/292; 422/295; 165/4; 165/108

(58) Field of Classification Search
 CPC .............. A61L 2/02; A61L 2/04; A61L 2/26; C02F 1/00; C02F 1/02; C02F 9/00; C02F 2009/00; C02F 2009/02; C02F 2303/00; C02F 2303/10
 USPC ................ 422/38, 310, 292, 295; 165/4, 108
 See application file for complete search history.

(56) References Cited

U.S. PATENT DOCUMENTS

| 4,708,849 | A | 11/1987 | Mielnik, Jr. et al. | 422/26 |
| 4,877,519 | A | 10/1989 | Robey | 210/86 |
| 6,521,133 | B1 | 2/2003 | Roediger | 210/742 |
| 6,656,423 | B1* | 12/2003 | Joslyn | 422/292 |
| 6,818,179 | B1* | 11/2004 | Edgson et al. | 422/38 |
| 2006/0018785 | A1* | 1/2006 | Bowen | 422/307 |
| 2007/0131603 | A1 | 6/2007 | Kantor et al. | 210/258 |

FOREIGN PATENT DOCUMENTS

| WO | WO 00/57928 | 10/2000 |
| WO | WO 03/031336 | 4/2003 |

OTHER PUBLICATIONS

European Search Report from a corresponding European patent application, namely, EP Appl. No. 11 39 7513.0, issued on Sep. 26, 2011. 5 pages.

* cited by examiner

*Primary Examiner* — Timothy Cleveland
(74) *Attorney, Agent, or Firm* — Kusner & Jaffe; Michael A. Centanni

(57) ABSTRACT

According to the present invention a method for heat recovery in a device for the sterilization of biological material is provided. The present method eliminates the risk of contaminating the sterilized effluent with unsterilized biological material via the heat recovery system. In a device according to the invention, a heat recovery circuit is provided for transferring heat from the sterilized effluent stream to the biologically hazardous feed stream. Protection against contamination through leaks is obtained by maintaining at all times a pressure difference preventing biologically hazardous material from bypassing the heat treatment and flowing in the direction of the sterilized material.

3 Claims, 1 Drawing Sheet

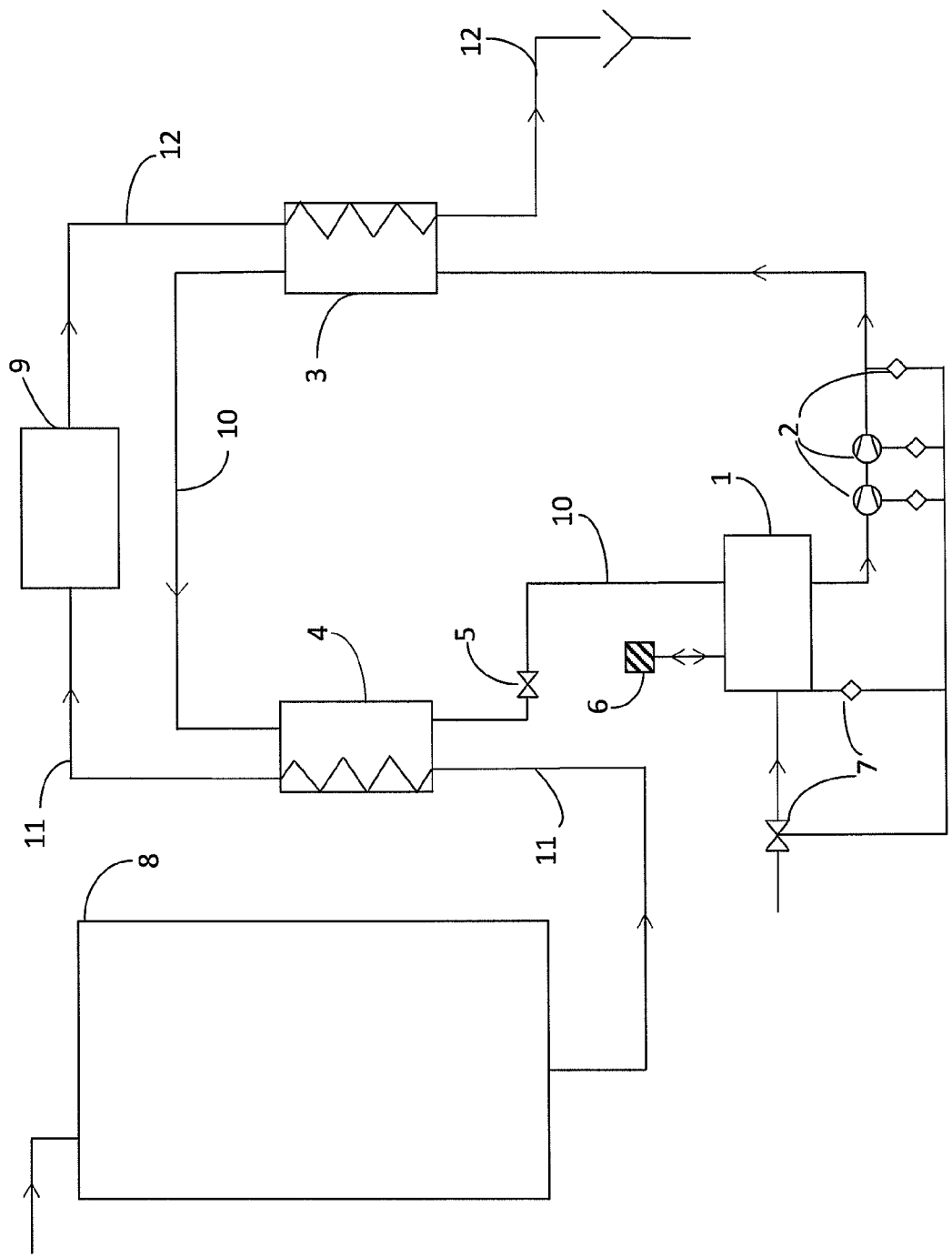

HEAT RECOVERY IN BIOWASTE STERILIZATION

FIELD OF THE INVENTION

The invention relates to improvement in heat recovery in a sterilization process for biological waste and to a device for implementing the method.

BACKGROUND OF THE INVENTION

Biological waste is produced e.g. in hospitals, agricultural or biological research and production facilities, plasma fractionation facilities, etc. Biological wastes produced in such facilities cannot be directly conducted to a sewer system, as these wastes often contain micro-organisms, such as bacteria, viruses and other microorganisms, which are hazardous to humans and animals. Prior to conducting to a sewer system, such biowaste must first be deactivated in a treatment plant designed for this purpose. For the treatment of biowaste, different treatment plants have been designed in which biowaste is sterilized prior to conducting to the sewer system. The sterilization of biowaste can be carried out chemically or by means of heat. The treatment plants can operate continuously or batchwise.

In an article by Carl J. Carlson in *Pharmaceutical Engineering*, May/June 2001, pages 70 to 82, facilities for the treatment of biowaste are described. The article deals with biowaste treatment facilities of different types as well as with dimensioning principles and problems relating thereto.

According to said article, a typical thermal continuous biowaste sterilisation apparatus comprises a separating unit for solid matter, a storage tank, a heating unit and a dwell circuit as well as a circulation circuit for circulating biowaste through said heating unit and said dwell circuit. According to the article, a typical continuous apparatus comprises the following stages: a heating stage, whereby biowaste is circulated in a heat exchanger and in a dwell circuit, until a temperature sufficient to kill the micro-organisms is reached. This is followed by an operating stage when the biowaste has reached the required temperature over the whole length of the heat exchanger. Thereby the treated biowaste is conducted through cooling equipment to a sewer system. If one or several sterilization parameters (temperature in the dwell circuit, pressure etc.) go outside the predetermined value, and the biowaste is therefore insufficiently sterilized, the process enters a hold state, where the biowaste is circulated through the heating unit and the dwell circuit until the parameter or parameters in question are again within the given limits. In case of an alarm, the apparatus enters the cooling mode, in which the operation of the heating unit is stopped, and the biowaste is recycled back to the pump feed line until the apparatus is again in working order. According to the article, provisions for the steam sterilization of the parts downstream from the storage tank should be provided, as well as provisions for preventing the transfer of the active biowaste to the cooling circuit. In addition, steam sterilization of the storage tank, the piping, venting filters, etc. should be provided in the apparatus.

Biowaste sterilization plants are usually provided with heat exchangers for cooling the effluent before it enters the sewer. The heat removed from the effluent stream is normally not utilized for feed preheating because of the safety issues involved with establishing a heat transfer connection between a sterilized stream and a biologically hazardous stream. A leak in a heat transfer loop may cause a serious risk of contamination.

The present invention provides heat recovery from the effluent stream without jeopardizing the integrity of the clean, or sterilized, stream and the equipment for handling it.

SUMMARY OF THE INVENTION

According to an aspect of the present invention, a method is provided for heat recovery in a device for the sterilization of biological material, said method eliminating the risk of contaminating the sterilized effluent with unsterilized biological material via the heat recovery system.

According to another aspect of the present invention, a device for the sterilization of biological material is provided comprising means for heat recovery, while ensuring that unsterilized biological material cannot enter the sterilized effluent via the heat recovery system.

In a device according to the invention, a heat recovery circuit is provided for transferring heat from the sterilized effluent stream to the biologically hazardous feed stream. Protection against contamination through leaks is obtained by maintaining at all times a pressure difference preventing biologically hazardous material from bypassing the heat treatment and flowing in the direction of the sterilized material.

BRIEF DESCRIPTION OF THE DRAWING

FIG. 1 is a schematic view of a device according to the invention, showing only the components required for the understanding of the invention.

DETAILED DESCRIPTION OF PREFERRED EMBODIMENT

An advantageous embodiment of the invention is described below with reference to the accompanying drawing.

The FIG. 1 shows a biowaste treatment apparatus according to the invention. The main components provided in the main line of the treatment apparatus in the flow direction of a biowaste-containing liquid are a storage tank 8 for the biowaste, a contaminated-feed line 11, a decontamination unit 9 and an exit line 12 for sterilized effluent. The decontamination unit comprises an appropriate number of pumps, heat exchangers, temperature and pressure sensors, valves and piping, none of which are shown but can be arranged as disclosed in e.g. EP 1 440 040. From the decontamination unit 9, a line 12 for sterilized effluent leads to the sewer.

In accordance with the present invention, the treatment apparatus comprises a heat recovery circuit comprising a break tank 1; at least one circulation pump 2; at least one heat recovery exchanger or effluent heat exchanger 3 for transferring heat from the effluent line 12 to the heat recovery circuit; at least one heat delivery exchanger or feed heat exchanger 4 for transferring heat from the heat recovery circuit to the contaminated-feed line 11; and interconnecting piping 10. The reference numeral 10 can be used in the following to refer either to the interconnecting piping or to the stream within the heat recovery circuit.

According to the invention, the pressure $p_{12}$ in the sterilized effluent line 12 is at all times higher than the pressure $p_{10}$ in the heat recovery circuit, and the pressure $p_{10}$ in the heat recovery circuit is at all times higher than the pressure $p_{11}$ in the contaminated-feed line 11. Thus, any movement of contaminated feed towards the sterilized effluent conduit is made impossible.

In principal the sterilization operation of biological material comprises three process stages; heating stage or start-up, operating i.e. sterilization stage and shutting down. In the context of this invention the term "all times" means these three process stages; start-up, sterilization and shut-down. In case one or several sterilization parameters go outside the predetermined value and the biowaste is therefore insufficiently sterilized, the process enters a hold state. During the operating stage the treated biowaste is conducted through cooling equipment to a sewer system. The most critical process stages as regards the risk of contamination through leaks, between the contaminated and sterilized water, are the start up and shut down. Therefore special care is taken during these stages. The sterilization process is started up as a closed system, during which the operability and safety of the process is ensured, especially the sufficiency of the decontamination and the critical pressures ($p_{10}$, $p_{11}$ and $p_{12}$) are determined and adjusted. The arrangement according to the present invention, shown in FIG. 1, i.e. the independent pressurized and pressure controlled heat transfer water loop ensures that the incoming contaminated feed cannot be in contact, not even indirectly, with the decontaminated effluent. Additionally, such pressure differential situations between these media are also avoided during the decontamination process. Further, the internal circulation (water loop) is protected by the pressure switch and pressure alarm and e.g. HEPA filter in the break tank 1.

Water enters the heat recovery circulation process from the break tank 1, which is preferably at atmospheric pressure. Air exchange from the break tank 1 is protected by, for example, a HEPA filter 6. The circulation pump 2a raises the pressure in the initial part of the heat recovery circuit to, for example, 3 bar. As shown in the FIGURE, a backup pump 2b is provided in case the first pump would fail or not produce the required pressure. The circulation pump 2a and the back-up pump 2b are shown in FIG. 1 with reference number 2. Preferably, the pumps are multistage centrifugal pumps, e.g. displacement pumps. Preferably, only one pump is used at a time.

In the heat recovery exchanger 3, having an effluent side and a heat recovery circuit side, the pressure $p_{12}$ on the effluent side 12 is kept at a higher level than in the heat recovery circuit, for example at 7 bar at the inlet, decreasing to for example 6 bar at the outlet assuming the pressure drop across the exchanger is of the order 1 bar. Correspondingly, the pressure $p_{10}$ on the heat recovery circuit side decreases to 2 bar in this example. The pressure $p_{12}$ on the effluent side 12 is typically kept at a minimum of 6 bar. The pressure $p_{10}$ on the heat recovery circuit side is kept at a minimum of 1 bar and at a maximum of 3 bar. Any internal leak in the exchanger would lead to sterilized effluent entering the heat recovery circuit, but not to heat recovery circuit water entering the sterilized effluent line.

In the heat delivery exchanger 4, having a feed side and a heat recovery circuit side, the pressure $p_{10}$ in the recovery circuit typically falls below 2 bar but is kept at a minimum of 1 bar, while the pressure $p_{11}$ on the side of the contaminated feed is no higher than 0.5 bar. Thus, at all times, the pressure $p_{10}$ in the heat recovery circuit is higher than the pressure $p_{11}$ in the contaminated feed line 11 and no contaminated feed will enter the heat recovery circuit in case of a leak within the heat delivery exchanger 4.

The pressure and flow rate in the heat recovery loop are determined by a fixed orifice 5, in addition to the pressure drops characteristic to the heat exchangers. Thus, when the performance of the pump 2 is according to specifications, the various pressure ratios within the heat recovery circuit remain permanent. After passing the fixed orifice 5, the water in the heat recovery circuit returns to the break tank 1. The water level of the break tank is maintained by means of valve 7, connected to a level sensor. If the pressure in the heat recovery circuit falls below the set lower limit e.g. 0.8 bar, the pressure switch will alert and stop the process. Thus, the means for maintaining the pressure in the heat recovery circuit side of the effluent heat exchanger (3) lower than the pressure in the effluent side (12); and the means for maintaining a pressure in the heat recovery circuit side of the feed heat exchanger (4) higher than the pressure in the feed side (11) comprise the pump (2), which induces the pressure, and the fixed orifice (5), which is used to determine the stream and by that way the counter pressure of the system; thus no other adjusting devices are needed.

The above described method for heat recovery in biowaste sterilization can be applied to both continuously and batch-wise operating sterilization processes.

In the above example, water is used as a heat transfer medium, but other heat transfer liquids are also possible. An indicator substance may be added to the heat recovery circuit to reveal leaks for example by a color change in the effluent.

Having described the invention, the following is claimed:

1. A method for recovering heat in a device for the sterilization of biological material, comprising
    passing a stream of biologically contaminated feed through a decontamination unit to produce a sterilized effluent stream, wherein the pressure ($p_{12}$) in the sterilized effluent stream is higher than the pressure ($p_{11}$) in the stream of biologically contaminated feed,
    transferring heat from the sterilized effluent stream to a stream in a heat recovery circuit, and
    transferring heat from the stream in the heat recovery circuit to the stream of biologically contaminated feed upstream of the decontamination unit,
    wherein the heat recovery circuit includes an orifice and a pump configured such that a portion of the heat recovery circuit is maintained at a pressure ($p_{10}$) that is between the pressure ($p_{11}$) in the stream of biologically contaminated feed and the pressure ($p_{12}$) in the sterilized effluent stream, and
    wherein a remaining portion of the heat recovery circuit is maintained at atmospheric pressure.

2. A method according to claim 1, wherein the pressure $p_{12}$ in the sterilized effluent stream is over 6 bar, the pressure $p_{10}$ in the heat recovery circuit is at minimum 1 bar and at maximum 3 bar, and the pressure $p_{11}$ in the stream of biologically contaminated feed is 0.5 bar or less.

3. A device for the sterilization of biological material, comprising:
    a feed line for contaminated material;
    an effluent line for sterilized material;
    a unit for heat treatment of said material, said unit for heat treatment having an inlet connected to said feed line for contaminated material and an outlet connected to said effluent line for sterilized material, wherein the decontamination unit is configured such that the pressure ($p_{12}$) in the effluent line is higher than the pressure ($p_{11}$) in the feed line;
    a heat recovery circuit for transferring heat from a stream in said effluent line to a stream in said feed line, said heat recovery circuit including an effluent heat exchanger having an effluent side and a heat recovery circuit side;
    a feed heat exchanger having a feed side and a heat recovery circuit side;
    piping connecting the heat recovery circuit sides of said heat exchangers;
    at least one pump for circulating a liquid through said heat recovery circuit;
    an orifice disposed in said heat recovery circuit at a location downstream of said feed heat exchanger and upstream of said at least one pump, wherein a pressure in the heat recovery circuit side of the effluent heat exchanger is maintained lower than the pressure in the effluent side and wherein a pressure in the heat recovery circuit side of the feed heat exchanger is maintained higher than the pressure in the feed side; and a break tank disposed at a location downstream of said orifice and upstream of said at least one pump, said break tank fluidly connected to a surrounding atmosphere and to a source of said liquid.

* * * * *